(12) United States Patent
Fontanet et al.

(10) Patent No.: US 10,660,419 B2
(45) Date of Patent: May 26, 2020

(54) PACKAGED SKIN TREATMENT COMPOSITION AND METHOD

(71) Applicant: ELC Management LLC, Melville, NY (US)

(72) Inventors: Osvaldo Fontanet, Fort Lee, NJ (US); Paul Abbatepaolo, Saint James, NY (US); Jennifer Fuller, Bronxville, NY (US); Jennifer Palmer Quintano, New York, NY (US); Snehal Shah, Neconset, NY (US); Mary Ann Smail, Commack, NY (US); Hua Wang, Islip, NY (US); Allan Hafkin, Plainview, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 15/598,430

(22) Filed: May 18, 2017

(65) Prior Publication Data

US 2018/0168316 A1  Jun. 21, 2018

Related U.S. Application Data

(60) Provisional application No. 62/434,717, filed on Dec. 15, 2016.

(51) Int. Cl.
*A45D 34/00* (2006.01)
*A45D 40/26* (2006.01)
(Continued)

(52) U.S. Cl.
CPC ........... *A45D 34/04* (2013.01); *A45D 34/045* (2013.01); *A45D 34/046* (2013.01);
(Continued)

(58) Field of Classification Search
CPC .. A45D 34/046; A45D 40/267; A45D 40/268; A45D 34/047
(Continued)

(56) References Cited

U.S. PATENT DOCUMENTS 2,173,959 A * 9/1939 Britt ..................... A45D 34/045
                                                        401/128
2,623,229 A * 12/1952 Brinton .................. A45D 34/02
                                                        401/128
(Continued)

FOREIGN PATENT DOCUMENTS

| CH | 705713 | 5/2013 |
|---|---|---|
| CN | 102973425 | 3/2013 |

(Continued)

OTHER PUBLICATIONS

Chun, et al.; Effect of molecular weight of hyaluronic acid (HA) on viscoelasticity and particle texturing feel of HA dermal biphasic fillers; Biomaterials Research; vol. 20; Article No. 24; pp. 1-7; Sep. 2016.

(Continued)

*Primary Examiner* — David P Angwin
*Assistant Examiner* — Bradley S Oliver
(74) *Attorney, Agent, or Firm* — Yonggang Wu

(57) ABSTRACT

A packaged skin treatment composition comprising:
(a) a receptacle with a neck and having stored therein a treatment composition containing microscopic three dimensional spherical structures having membranous outer walls and secluded internal spaces,
(b) a wiper affixed within the neck and having an internal barrel portion,
(c) a closure for the receptacle,
(d) an applicator comprised of a rod with a proximal end affixed to the closure and a distal end terminating in an enlarged portion, (Continued)

wherein when the rod is extracted from the receptacle the treatment composition loads onto the applicator in an amount sufficient to permit application of the treatment composition containing the microscopic spherical structures to the treatment surface.

19 Claims, 8 Drawing Sheets

Specification includes a Sequence Listing.

(51) Int. Cl.
| | |
|---|---|
| *A61Q 19/00* | (2006.01) |
| *A61K 8/02* | (2006.01) |
| *A61Q 1/02* | (2006.01) |
| *A61Q 19/08* | (2006.01) |
| *A61K 8/73* | (2006.01) |
| *A61K 8/81* | (2006.01) |
| *A61K 8/87* | (2006.01) |
| *A61K 8/88* | (2006.01) |
| *A45D 34/04* | (2006.01) |

(52) U.S. Cl.
CPC ......... *A45D 40/262* (2013.01); *A45D 40/265* (2013.01); *A45D 40/267* (2013.01); *A61K 8/0204* (2013.01); *A61K 8/025* (2013.01); *A61K 8/0208* (2013.01); *A61K 8/0212* (2013.01); *A61K 8/731* (2013.01); *A61K 8/733* (2013.01); *A61K 8/735* (2013.01); *A61K 8/8129* (2013.01); *A61K 8/8147* (2013.01); *A61K 8/8152* (2013.01); *A61K 8/87* (2013.01); *A61K 8/88* (2013.01); *A61Q 1/02* (2013.01); *A61Q 19/00* (2013.01); *A61Q 19/005* (2013.01); *A61Q 19/08* (2013.01); *A61K 2800/412* (2013.01); *A61K 2800/87* (2013.01)

(58) Field of Classification Search
USPC .................................................. 401/122, 128
See application file for complete search history.

(56) References Cited

U.S. PATENT DOCUMENTS

| | | | | |
|---|---|---|---|---|
| 2,681,463 | A * | 6/1954 | Gordon ................. | B65D 51/32 |
| | | | | 401/128 |
| 3,439,088 | A | 4/1969 | Edman | |
| 3,818,105 | A | 6/1974 | Coopersmith et al. | |
| 3,867,352 | A | 2/1975 | Akamatsu et al. | |
| 4,960,339 | A | 10/1990 | Iizuka et al. | |
| 5,077,211 | A | 12/1991 | Yarosh | |
| 5,190,389 | A | 3/1993 | Vasas | |
| 5,190,762 | A | 3/1993 | Yarosh | |
| 5,272,079 | A | 12/1993 | Yarosh | |
| 5,296,231 | A | 3/1994 | Yarosh | |
| 5,324,128 | A | 6/1994 | Gueret | |
| 5,346,935 | A | 9/1994 | Suzuki et al. | |
| 5,599,125 | A | 2/1997 | Vasas et al. | |
| 5,816,728 | A * | 10/1998 | Nardolillo ............ | A45D 40/265 |
| | | | | 401/126 |
| 6,010,265 | A * | 1/2000 | Bouix .................. | A45D 40/267 |
| | | | | 401/121 |
| 6,076,985 | A | 6/2000 | Gueret | |
| 6,168,334 | B1 * | 1/2001 | Fordham .............. | A45D 34/046 |
| | | | | 401/121 |
| 6,197,319 | B1 | 3/2001 | Wang et al. | |
| 6,270,273 | B1 * | 8/2001 | Ohba ................... | A45D 34/047 |
| | | | | 401/122 |
| 6,298,864 | B1 | 10/2001 | Gueret | |
| 6,375,374 | B2 * | 4/2002 | Gueret ................ | A45D 40/267 |
| | | | | 401/121 |
| 6,685,963 | B1 | 2/2004 | Taupin et al. | |
| 7,182,535 | B2 * | 2/2007 | Lim ..................... | A45D 40/267 |
| | | | | 401/122 |
| 7,654,998 | B1 | 2/2010 | Ingenito | |
| 7,687,574 | B2 | 3/2010 | Lu et al. | |
| 7,833,541 | B2 | 11/2010 | Lu et al. | |
| 7,967,519 | B2 | 6/2011 | Gueret | |
| 7,972,073 | B2 * | 7/2011 | Vintimiglia .......... | A45D 40/267 |
| | | | | 401/126 |
| 8,104,985 | B2 * | 1/2012 | Manici ................. | A45D 40/267 |
| | | | | 401/122 |
| 8,721,210 | B2 | 5/2014 | Wilcyzynski | |
| 2009/0071498 | A1 | 3/2009 | Tranchant | |
| 2009/0155371 | A1 * | 6/2009 | Sojka ................... | A61K 8/0275 |
| | | | | 424/497 |
| 2009/0220481 | A1 | 9/2009 | Maes et al. | |
| 2011/0243983 | A1 | 10/2011 | Paufique | |
| 2011/0256059 | A1 | 10/2011 | Sanchez Barreiro et al. | |
| 2011/0262489 | A1 | 10/2011 | Zhao | |
| 2012/0172457 | A1 | 7/2012 | Braun et al. | |
| 2012/0279876 | A1 * | 11/2012 | Weigel ................. | A45D 40/265 |
| | | | | 206/1.5 |
| 2012/0295870 | A1 | 11/2012 | Lebreton | |
| 2014/0147189 | A1 * | 5/2014 | Wightman ............ | A45D 40/267 |
| | | | | 401/122 |
| 2014/0179640 | A1 | 6/2014 | Weinberger et al. | |
| 2015/0164770 | A1 | 6/2015 | Somerville et al. | |
| 2016/0030328 | A1 | 2/2016 | Mohammadi et al. | |
| 2016/0174689 | A1 | 6/2016 | Wilczynski | |

FOREIGN PATENT DOCUMENTS

| | | | |
|---|---|---|---|
| CN | 104473786 | 4/2015 | |
| CN | 105233270 | 1/2016 | |
| CN | 105250184 | 1/2016 | |
| CN | 106137918 | 11/2016 | |
| CN | 106176688 | 12/2016 | |
| DE | 10-200805390 | 4/2015 | |
| EP | 0516026 | 12/1992 | |
| EP | 1360955 | 11/2003 | |
| EP | 2798974 | 11/2014 | |
| FR | 3028731 | 5/2016 | |
| FR | 3065358 A3 * | 10/2018 | ........... A45D 40/267 |
| JP | 2004/210765 | 7/2004 | |
| WO | WO-2014/044808 | 3/2014 | |
| WO | WO-2016/062888 | 4/2016 | |

OTHER PUBLICATIONS

Goodman, et al; "An Interesting Reaction to a High and Low Molecular Weight Combination Hyaluronic Acid"; Letter and Communications; American Society for Dermatologic Surgery, Inc.; pp. S164-S166; 2015.

Lee, et al.; Effects of Low and High Molecular Weight Hyaluronic Acids on Peridural Fibrosis and Inflammation in Lumbar Laminectomized Rats; The Korean Journal of Pain; vol. 24; No. 4; pp. 191-198; Dec. 2011.

Lochhead, Robert Y; "Features Trends in Polymers for Skin Care, Part I"; HAPPI; 6 pps; Mar. 2009.

Mintel; http://www.gndp.com; Flash Dazzling Skin Ampoules; Record ID: 2542255; Laboratorious Marti Tor; Marti Derm La Formula; Skincare; Face/Neck Care; Spain; Jul. 2014.

Mintel; http://www.gnpd.com; Bio Cellulose Mask; Record ID: 2891365; It's More; Bio Suppu; Skincare; Face/Neck Care; Japan; Jan. 2015.

Mintel; http://www.gnpd.com; Black Rose Skin Regenerating Goodnight Mask; Record ID: 3453543; Krystyna Janda; Janda; Skincare; Face/Neck Care; Poland; Sep. 2015.

Mintel; http://www.gnpd.com; Boost Integral Revitalizing Supplement Serum: Record ID: 2751013; Immanence Integral Dermo Correction; IDC + Regen; Skincare; Face/Neck Care; France; Jul. 2015.

Mintel; http://www.gnpd.com; Face and Body Sunscreen Cream SPF 15; Record ID: 4166341; Planter's; Planter's Cosmetica Naturale Hyaluronic Acid Anti-Age; Skincare; Sun-Sun/Sunbed Exposure; Netherlands; Jul. 2016.

(56) References Cited

OTHER PUBLICATIONS

Mintel; http://www.gnpd.com; Instant Lifting Serum + Continual Integral Correction; Record ID: 3926305; Immanence Integral Dermo Correction; Immanence Integral Dermo Correction; IDC + Ideal Multi-Correction; Skincare; Face/Neck Care; France; May 2016.

Mintel; http://www.gnpd.com; Long Serum Mascara; Record ID: 2392551; Styling Life Holdings—Japan; Cavanne; Colour Cosmetics—Eye Colour Cosmetics—Eye Lash; Japan; May 2014.

Mintel; http://www.gnpd.com; Perfect Gel Foundation SPF40 PA+++; Record ID: 2882037; Dr. Ci;Labo; Dr. Ci:Labo; Colour Cosmetics; Face Colour Cosmetics—Foundations/Fluid Illuminators; Japan; Jan. 2015.

Mintel; http://www.gnpd.com; Perfect Water Cool SPF 50+/PA++++; Record ID: 2661205; Isehan; Kiss Me by Isehan Sunkiller; Skincare; Sun—Sun/Sunbed Exposure; Japan; Feb. 2014.

Mintel; http://www.gnpd.com; S.O.S. Thirst-Quenching Serum; Record ID: 1787915; Caudalie; Caudalie Vinosource; Skincare; Face/Neck Care; USA; Apr. 2012.

PCT Int'l Search Report; Int'l Application No. PCT/US2017/064757; Completion Date: Feb. 27, 2018; dated Feb. 27, 2018.

PCT Int'l Search Report; Int'l Application No. PCT/US2017/064764; Completion Date: Apr. 18, 2018; dated Apr. 18, 2018.

PCT Written Opin of the Int'l Searching Authority; Int'l Application No. PCT/US2017/064757; Completion Date: Feb. 27, 2018; dated Feb. 27, 2018.

PCT Written Opin of the Int'l Searching Authority; Int'l Application No. PCT/US2017/064764; Completion Date: Apr. 18, 2018; dated Apr. 18, 2018.

Supplementary European Search Report; EP Application No. 17880149.4; Completion Date: Oct. 29, 2019; dated Nov. 11, 2019.

Supplementary European Search Report: EP Application No. 17881085.9: Completion Date: Jan. 10. 2020; dated Jan. 24. 2020.

\* cited by examiner

SEQUENCE LISTING

```
<160> NUMBER OF SEQ ID NOS: 7

<210> SEQ ID NO 1
<211> LENGTH: 13
<212> TYPE: PRT
<213> ORGANISM: Artificial Sequence
<220> FEATURE:
<223> OTHER INFORMATION: CLOCK and/or PER1 gene activator
<220> FEATURE:
<221> NAME/KEY: misc_feature
```

```
<222> LOCATION: (1)..(4)
<223> OTHER INFORMATION: Xaa can be any naturally occurring amino acid
      or no amino acid
      220>
<221> NAME/KEY: misc_feature
<222> LOCATION: (5)
<223> OTHER INFORMATION: Xaa can be threonine or serine or no amino acid
<220> FEATURE:
<221> NAME/KEY: misc_feature
<222> LOCATION: (9)
<223> OTHER INFORMATION: Xaa can be isoleucine, leucine, proline,
      valine, alanine, glycine or no amino acid
<220> FEATURE:
<221> NAME/KEY: misc_feature
<222> LOCATION: (10)..(13)
<223> OTHER INFORMATION: Xaa can be any naturally occurring amino acid
      or no amino acid

<400> SEQUENCE: 1

Xaa Xaa Xaa Xaa Xaa Ser Thr Pro Xaa Xaa Xaa Xaa Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CLOCK and/or PER1 gene activator

<400> SEQUENCE: 2

Tyr Val Ser Thr Pro Tyr Asn
1               5

<210> SEQ ID NO 3
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 3

Val Ser Thr Pro Glu
1               5

<210> SEQ ID NO 4
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 4

Leu His Ser Thr Pro Pro
1               5

<210> SEQ ID NO 5
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 5

Arg His Ser Thr Pro Glu
1               5

<210> SEQ ID NO 6
<211> LENGTH: 5
<212> TYPE: PRT
```

```
<213> ORGANISM: Artificial Sequence
<220> FEATURE:
<223> OTHER INFORMATION: CLOCK and/or PER1 gene activator

<400> SEQUENCE: 6

His Ser Thr Pro Glu
1               5

<210> SEQ ID NO 7
<211> LENGTH: 4
<212> TYPE: PRT
<213> ORGANISM: Artificial Sequence
<220> FEATURE:
<223> OTHER INFORMATION: CLOCK and/or PER1 gene activator

<400> SEQUENCE: 7

Ser Pro Leu Gln
1
```

PACKAGED SKIN TREATMENT COMPOSITION AND METHOD

TECHNICAL FIELD

The invention is in the field of a packaged skin treatment composition where formula, dose, applicator, and application method interact to optimize the end benefit to be achieved. In addition, the product is designed so that the consumer's intuitive use of the product will naturally correlate with manufacturer instructions for correct use even if those instructions are not read.

BACKGROUND OF THE INVENTION

When treating skin to achieve benefits, the success of the end result depends on many different factors. While the formula of the treatment composition is important, it is not the only thing that contributes to a successful and consumer perceptible end result. Also important is ensuring that the correct amount of treatment composition is applied to the treatment surface, and that it is applied in a way that optimizes its end benefits. For example, it is known that consumers often do not read directions on products they buy. As a result, the products are applied incorrectly or in improper amounts. The end result is that the product is not as effective as it could be and the consumer may reach the conclusion that it is not effective for its intended purpose. One way to address this problem is to design packaged products so that the consumer's intuitive use of the product is correct and in accordance with product instructions even if the consumer did not read them.

When considering eye treatment compositions in particular, most often the desired end benefits are to reduce the appearance of superficial lines and wrinkles around the eyes, to lift and tighten loose or baggy skin under eye skin, and to lighten the appearance of dark under eye circles. Lifting and tightening skin under the eyes can significantly reduce the perception of aging by providing the fresh, "wide open eye" look of youth.

It has been discovered that formulating eye treatment compositions in a way that causes the polymers present in the composition to "ball up" will facilitate formation of a physical "micro-mesh" structure within the formula that will lift, tighten, and plump under eye skin. It has been further discovered that the desired benefit is optimized when the appropriate dose of treatment composition is applied to the treatment surface and even further improved when applied with a specially designed applicator using a massaging effect.

The invention is directed to packaged skin treatment product comprising a skin treatment composition, a receptacle for storing the composition and an applicator in the form of a cap/rod/applicator assembly, where the amount of product delivered is appropriate and the suggested regimen maximizes the end benefit.

SUMMARY OF THE INVENTION

The invention is directed to a packaged skin treatment composition comprising:
  (a) a receptacle with a neck and having stored therein a treatment composition containing microscopic three dimensional spherical structures having membranous outer walls and secluded internal spaces,
  (b) a wiper affixed within the neck and having an internal barrel portion,
  (c) a closure for the receptacle,
  (d) an applicator comprised of a rod with a proximal end affixed to the closure and a distal end terminating in an enlarged portion,
wherein when the rod is extracted from the receptacle the treatment composition loads onto the applicator in an amount sufficient to permit application of the desired amount of the treatment composition containing the microscopic spherical structures to the treatment surface.

The invention is also directed to a method for applying a treatment composition containing microscopic three dimensional spherical structures having membranous outer walls and secluded internal spaces to the skin comprising the steps of:
  (a) Storing the treatment composition in a receptacle with a neck and a wiper affixed within the neck having an internal barrel portion, a closure for the receptacle and an applicator comprised of a rod with a proximal end affixed to the closure and an a distal end terminating in an enlarged portion,
  (b) Extracting the applicator from the receptacle and loading the treatment composition thereon,
  (c) Applying the treatment composition containing the microscope three dimensional spherical structures to the skin with the applicator.

DETAILED DESCRIPTION

I. Definitions

All percentages mentioned herein are percentages by weight unless otherwise indicated.

All documents mentioned herein are incorporated by reference in their entirety.

"Micro-mesh" means three dimensional spherical structures having membranous outer walls that e interlocked in association to form a network when in concentrate. The membranous outer walls of the spherical structure form an internal space within the sphere that is secluded from the surrounding environment and the contents of the interlocked spheres. When incorporated into a topical composition the Micro-mesh may remain in concentrated form or it may be diluted.

The term "Scanning Electron Microscope (SEM)" means that a microscope scans a sample with a focused electron beam and delivers images with information about the sample topography and composition.

II. The Packaged Composition

The various components of the packaged composition will be further described herein.

A. The Receptacle

Figure 1A:
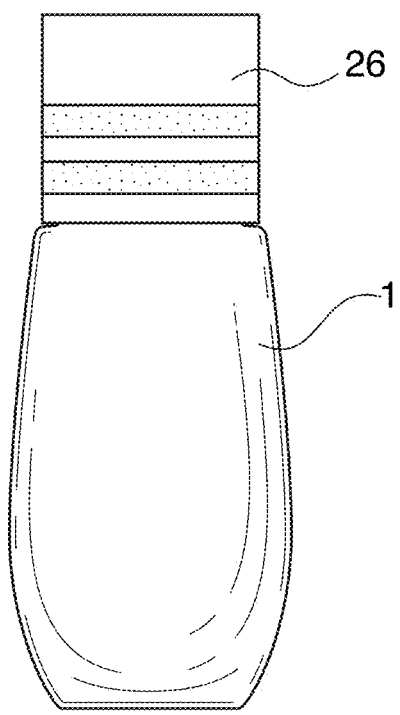
FIG. 1A depicts a plan view of a type of receptacle for use in storing the treatment composition.
Figure 1B:
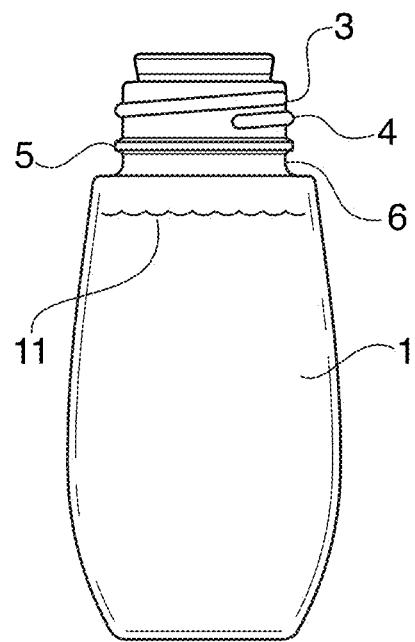
FIG. 1B depicts a cross-sectional view of the receptacle in FIG. 1 with closure removed and showing treatment composition inside.
Figure 1C:
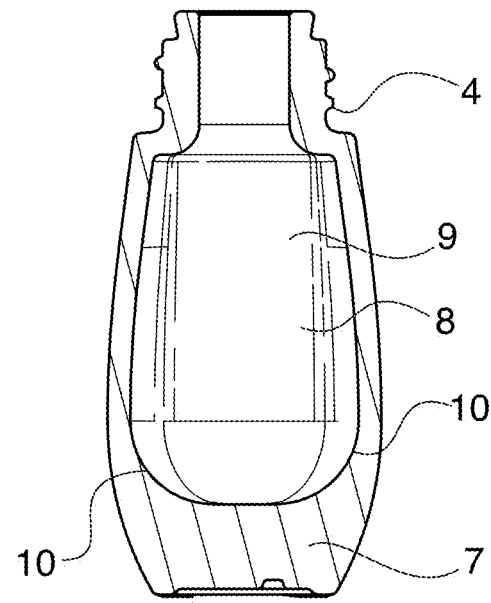
FIG. 1C is a cross-sectional view similar to FIG. 1B except with treatment composition removed, showing the base of the receptacle having additional weight and thickness and the interior portion of the receptacle where the treatment composition is stored.

The receptacle 1 is depicted in FIG. 1 and may be made of glass or plastic. The receptacle having a closure 26 thereon is seen in FIG. 1A. The receptacle without a closure and showing fill with the treatment composition 11 is seen in FIG. 1B. Receptacle has a neck 3 with threads 4 to facilitate engagement with corresponding threads on inner surface of closure 26. If desired, neck 3 contains a stop 5 in the form of a circumferential bead around the base 6 of the neck 3 to enable securing closure 26 in proper location when the receptacle 1 is closed. In one preferred embodiment receptacle 1 is made of glass and, as depicted in FIG. 1C has a base portion 7 that is solid glass of a thickness and diameter sufficient to weight the receptacle 1 to stand upright and resist breakage when dropped. More preferred is where the receptacle 1 is glass and the internal space 8 for storage of the treatment composition is oblong 9 with rounded sides 10. To optimize the delivery of the treatment composition 11, the volume, area, and dimensions of internal space 8 correlates with the applicator (to be discussed later).

In the event the receptacle 1 is made of plastic, suitable plastics include Bis-phenol A (BPA), polyethylene, polypropylene, or the like.

B. The Wiper

Figure 2A:
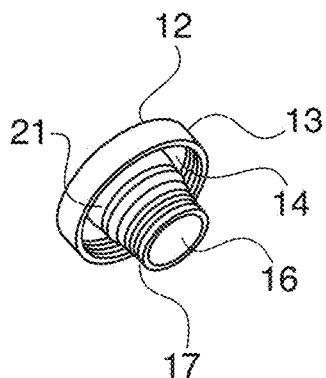
FIG. 2A is a perspective view of the wiper.
Figure 2B:
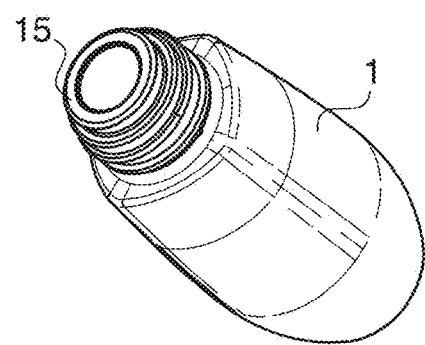
FIG. 2B is a top plan view of the receptacle showing how the wiper fits into the neck of the receptacle.
Figure 2C:
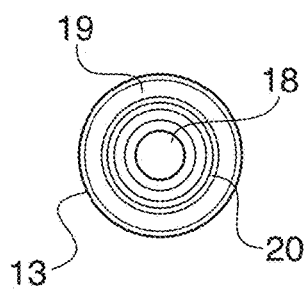
FIG. 2C is a top plan view of the wiper top surface showing the orifice from which the applicator is extracted.
Figure 2D:
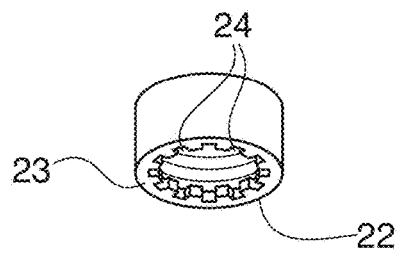
FIG. 2D is a cutaway view of the bottom section of the wiper showing the holes around the circumference of the wiper.
Figure 2E:
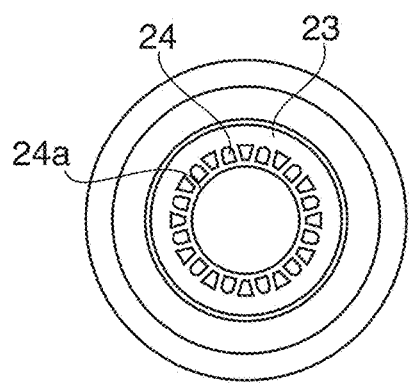
FIG. 2E is a magnified plan view of the wiper bottom orifice showing the holes.
Figure 2F:
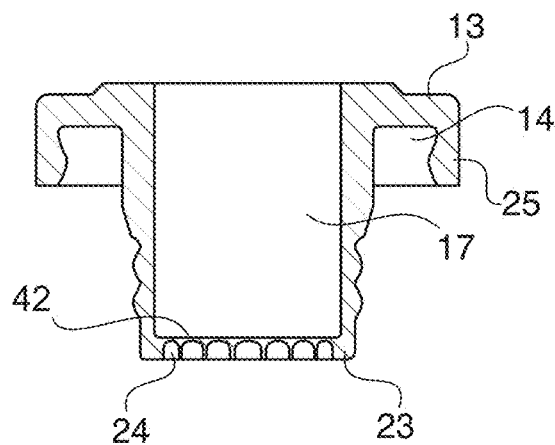
FIG. 2F is a cross-sectional view across the mid-section of the wiper showing the holes in the shelf, the side walls and the arms.

The receptacle 1 contains a neck 3. Seated within neck 3 is a wiper 12 as best depicted in FIG. 2. Wiper 12 is made of a pliable thermoplastic material such as low density polyethylene (LDPE) so it has sufficient flexibility to enable fitting into the neck 3 of receptacle 1 and remain in place even when the applicator 35 is removed from the receptacle 1. FIG. 2A is a perspective view of wiper 12 showing a collar 13 that creates a circumferential depression 14 that enables wiper 12 to seat onto neck 3 as depicted by numeral 15 in FIG. 2B which shows a top perspective view of the receptacle 1 with wiper 12 seated in neck 3. Also seen in FIG. 2A is the barrel portion 16 of wiper 12 which is formed by downwardly extending circumferential walls 17. The orifice 18 of wiper 12 is shown in FIG. 2C which is a top plan view of the wiper 12 showing the top flat edge 19 of collar 13 and circumferential rings 20. If desired, an area of increased thickness or a ridge 21 is found directly beneath collar 13 on wiper 12 to better facilitate seating of wiper 12 in neck. FIG. 2D shows a sectional view of sectional walls 17 and the distal portion 22 which has a shelf 23 having holes or serrations 24. Preferably the holes or serrations 24 are evenly spaced around the shelf 23. The purpose of such holes or serrations 24 is to permit the treatment composition 11 to seep into the barrel portion 16 and be stored there. This facilitates loading of the optimal amount of the treatment composition 11 onto the applicator 35 from the receptacle 1. FIG. 2E is a bottom plan magnified view of the wiper showing the shelf 23 with holes 24. FIG. 2F is a side cutaway view of the wiper showing the collar 13 which has downward projecting arms 25 that form a circumferential depression 14 and downwardly extending walls 17 that terminate in the shelf 23 with holes 24. Holes 24 have an external border 24A extending around the circumference of the shelf 23 facing the orifice 18. Holes 24 provide at least two benefits. The first is that holes 24 permit seepage of treatment composition 11 into the barrel portion 16 of wiper. In addition, holes 24 having external border 24A enable wiper orifice 18 to accommodate applicator 35 enlarged portion 38 to be extracted from the receptacle 1 even when diameter of orifice 18 is smaller than diameter of enlarged portion 38. The holes or serrations 24 may or may not penetrate through the shelf 23. In one preferred embodiment, orifice 18 has a cross-sectional diameter of 5.25 to 7.25 millimeters, and is preferably about 6.25 millimeters which is smaller than the cross-sectional diameter of applicator 35 enlarged portion 38, which ranges from 5.6 to 6.6 millimeters with 6.5 millimeters being most preferred. As will be later explained this provides a wiping effect that optimizes placement of the treatment composition 11 load onto the rod 37 and enlarged portion 38.

C. The Closure

Figure 3A:
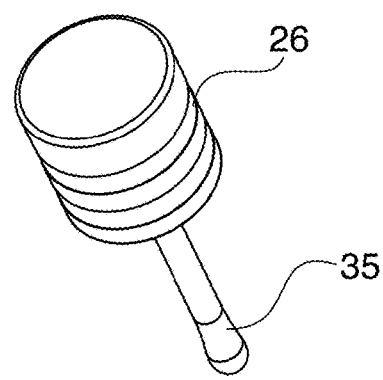
FIG. 3A is a perspective view of the closure.
Figure 3B:
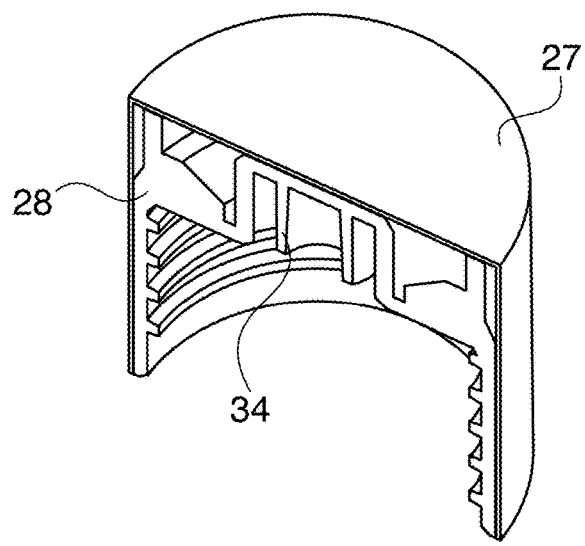
FIG. 3B is a cutaway view of the closure showing the outer shell and inner cap in configuration.
Figure 3C:
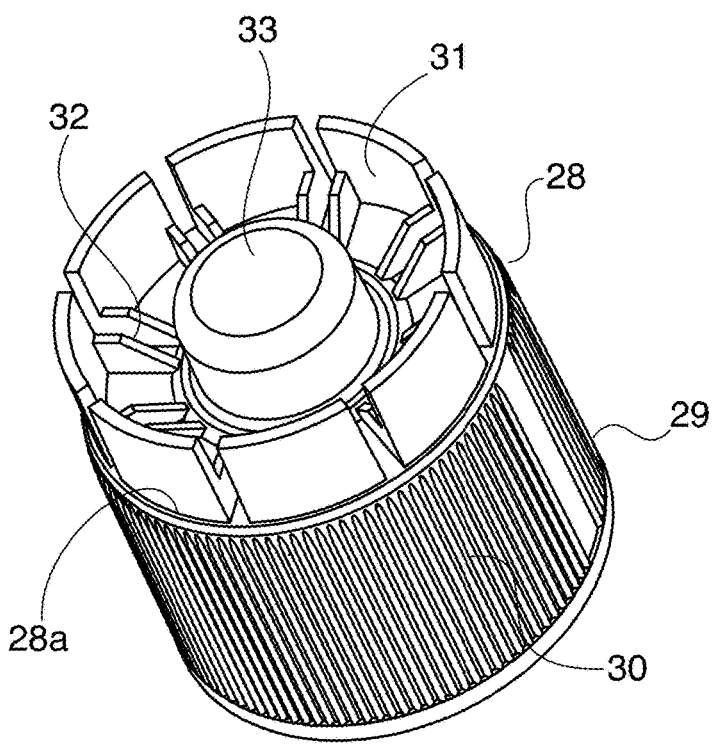
FIG. 3C is a perspective view of the inner cap.
Figure 3D:
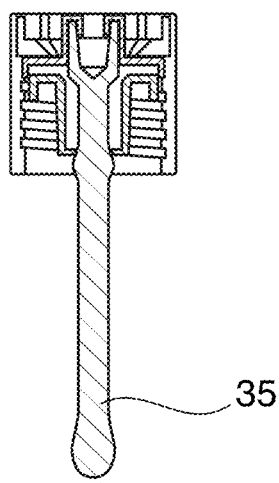
FIG. 3D is a cross-sectional view across the mid-section of closure showing the outer shell, inner cap, and applicator.
Figure 3E:
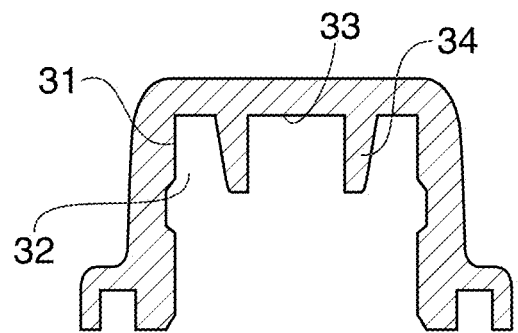
FIG. 3E is a top half cross-sectional view of the inner cap.

The receptacle has a closure 26. A perspective view of the closure 26 is seen in FIG. 3A. Closure comprises a cap shell 27 that forms the decorative outer surface of the cap that is visible to the consumer. Cap shell 27 fits over outer surface 29 of inner cap 28 which is shown in FIGS. 3B and 3C. Inner cap 28 preferably has circumferential downwardly extending ribs 30 that facilitate holding of cap shell 27 securely on inner cap 28. The upper surfaces of ribs 30 terminate in a bead 28A that extends the circumference of the inner cap 28. Extending above bead 28A and ribs 30 are a series of upwardly extending panels 31 held in place by struts 32 which connect panels 31 to a central core 33 having side and top walls. The underside of central core 33 is hollow and has a downwardly extending wall 34 that permits engagement of the applicator 35 to the inner cap 28.

D. The Applicator

Figure 4A:
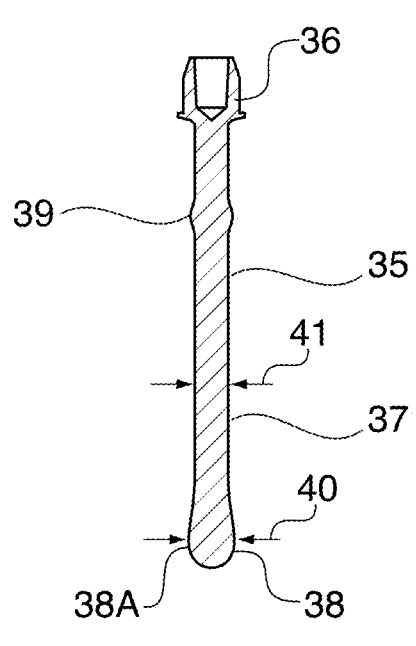
FIG. 4A depicts a cross-sectional view taken across the mid-section of the applicator of FIG. 4B.
Figure 4B:
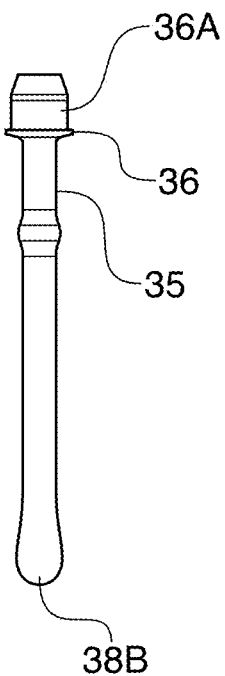
FIG. 4B shows a plan view of the applicator.

The applicator 35 is best seen in FIG. 4. FIG. 4A shows the applicator 35 in cross-section. FIG. 4B shows a plan view of the applicator 35. Proximal end of applicator 35 has a gate 36 and extending upwardly from gate 36 a head and neck 36A. Head and neck 36A mate with downwardly extending walls 34 on underside of central core 33 and hold applicator 35 securely in inner cap 28 and closure 26.

Applicator is comprised of a rod 37 and a distal enlarged portion 38. If desired, applicator 35 rod 37 contains an enlarged circumferential band 39 which may serve as a stop to prevent the treatment composition 11 from loading too high up on rod 37 and interfering with closure of the receptacle 1. Applicator 35 rod 37 has a cross-sectional diameter 41 and distal enlarged portion has a cross-sectional diameter 40. In one preferred embodiment the cross-sectional diameter 41 ranges from 4.5 to 5.5 millimeters with 5 millimeters being most preferred; and cross-sectional diameter 40 ranges from 5.6 to 6.6 millimeters with 6.5 millimeters being most preferred. Stated another way it has been discovered that when cross-sectional diameter 40 of enlarged portion 38 is from 25 to 45% larger than cross-sectional diameter 41 of rod 37 the optimum amount and placement of treatment composition 11 is loaded onto the applicator 35. Applicator 35 is most preferably made of plastic, in particular, plastics from the polyester family. It is preferred that the plastic be clear or translucent. According polyethylene terephthalate (PET) or polyethylene terephthalate glycol (PETG) are most preferred. The plastic used should be bendable to permit applicator to be used to "sweep" inner sides of receptacle 1 to collect treatment composition 11 that may have lodged there and would otherwise be unavailable for application to the treatment surface.

E. The Method

Figure 5A:
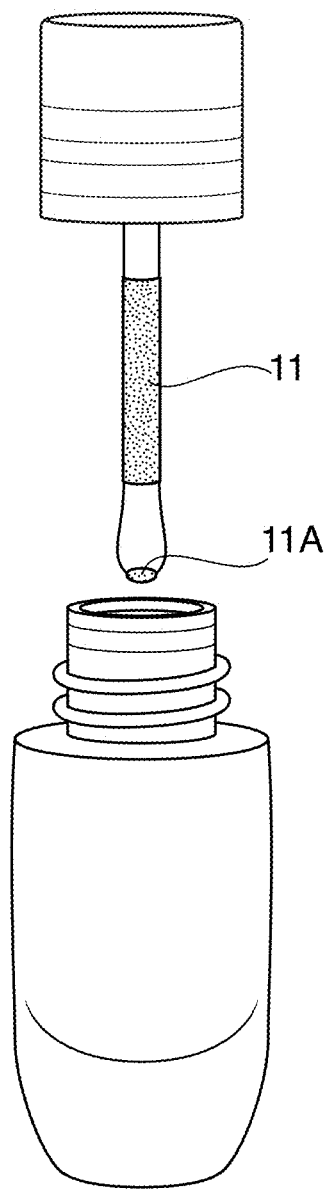
FIG. 5A shows how the treatment composition loads onto the applicator when it is extracted from the receptacle by the user.

As best depicted in FIG. 5A, when the consumer uses the product, the closure 26 is removed from the receptacle. The applicator 35 is withdrawn from the receptacle 1 by extracting the applicator 35 through wiper 12. Enlarged portion 38 of applicator 35 is extracted through orifice 18 of wiper and because enlarged portion 38 is larger in cross-sectional diameter 40 than orifice 18 the sides 38A of enlarged portion 38 are wiped leaving very little if any treatment composition on the sides of enlarged portion 38. However, due to holes 24 in shelf 23 surrounding orifice 18 treatment composition 11 seeps into the cavity formed by wiper barrel portion 16 and will load onto rod 37. Since rod 37 is much smaller in diameter than orifice, when applicator 35 is extracted from wiper 12 the rod 37 contains a load of treatment composition, while the sides of enlarged portion 38 of applicator 35 are wiped clean, and there is a small dollop 11A of treatment composition 11 left on the distal surface 38B of enlarged portion 38. The amount of treatment composition 11 loaded onto the applicator 35 is preferably sufficient for treating the application surface. In addition, the placement of the treatment composition 11 on the rod 37 and very distal tip 38A of enlarged portion dictates how the consumer will intuitively apply the dose to the treatment surface.

Figure 5B:
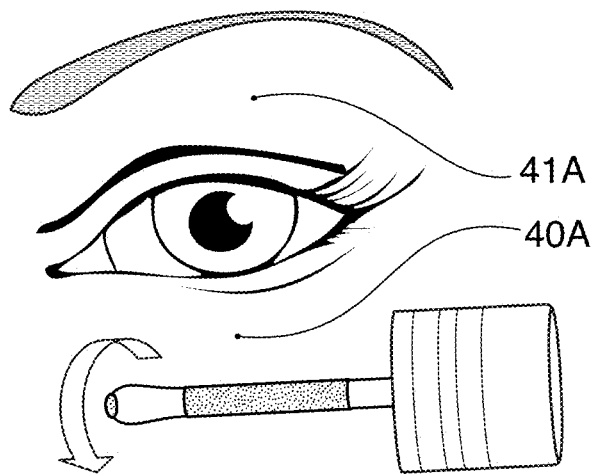
FIG. 5B demonstrates how the treatment composition is applied to the under eye area by rolling the rod axial surface across the lower eyelid to apply the treatment composition.

In particular, the rod 37 containing the loaded treatment composition 11 is placed cross-wise across the under eye as depicted in FIG. 5B. The rod 37 is rolled one or more times to cause the treatment composition 11 to apply to the under eye area 40A. The dollop 11A of treatment composition 11 may be used to treat the upper eyelid 41A. After application of the treatment composition 11 the enlarged portion 38 is used as a massage tool to massage the treatment composition 11 onto skin of the under eye area 40 and the upper eyelid area 41. In addition to distributing the load of treatment composition 11 over the desired treatment surfaces the massaging application also improves blood flow into the eye area, causing a physical skin plumping and improved penetration of the treatment composition 11.

F. The Treatment Composition

The treatment composition may be in the form of an emulsion, aqueous solution or dispersion, gel, or anhydrous composition. The treatment composition contains three dimensional spherical structures having membranous outer walls and an internal space within the sphere that is secluded from the surrounding environent. The spherical structures are formed when one or more polymers in the formula "ball up" by reacting with other constituent portions on the polymer or other ingredients in the composition to for structures having membranous outer walls protecting an internal space. A suitable method for testing whether the polymers to be formulated into the treatment composition will form the desired micro-mesh structure is simple and can be determined by combining, in water, the polymer and an anionic non-sulfated glycoaminoglycan which is a long unbranched polysaccharides containing repeating disaccharide units. The repeating units are amino sugars such as glucosamine or galactosamine and glucuronic acid or galactose. Hyaluronic acid is particularly suitable.

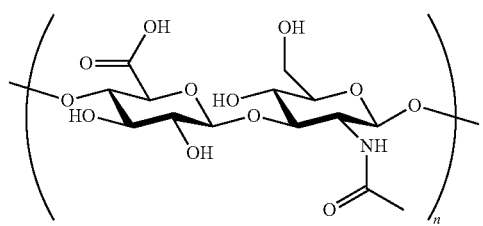

Hyaluronic Acid

In order to identify polymers that will form the desired mesh the polymer and the glycosaminoglycan are combined in water. One particularly suitable test is to combine from 0.01 to 5% of the polymer with 0.01 to 5% of the glycosaminoglycan, hyaluronic acid in particular, in water and evaluate the formation of the micro-mesh, e.g. the three dimensional spherical structures having membranous outer walls that are interlocked in association to form a network. The membranous outer walls of the spherical structures form an internal space within the sphere that is secluded from the surrounding environment.

After determination that a micro-mesh is formed, the micro-mesh ingredients are formulated into the treatment composition.

Polymers that are suitable for micro-mesh formation include, but are not limited (1). The Polymer Used to Form the Micro-Mesh (the "Polymer")

The treatment composition comprises at least one Polymer as further defined herein. Suggested amounts of the Polymer may range from 0.001 to 10%, preferably 0.01 to 5% and more preferably 0.05 to 1.0% by the weight of total composition. In addition to the Polymers recited below, other suitable polymers that form the desired micro-mesh structure can be identified by combining the test polymer the glycosaminoglycan, most preferably hyaluronic acid (HA). The HA may be low molecular weight, high molecular weight, or mixtures of both. Low molecular weight HA (LMW HA) has a molecular weight ranging from $1\times10^3$ Dalton to $8\times10^5$ Dalton, preferably from $5\times10^3$ Dalton to $1\times10^5$ Dalton, more preferably from $8\times10^3$ Dalton to $5\times10^4$ Dalton.

The HA may also be high molecular weight (HMW HA), having a $8\times10^5$ Dalton to $1\times10^7$ Dalton, preferably from $1\times10^6$ Dalton to $8\times10^6$ Dalton, more preferably from $1.2\times10^6$ Dalton to $3\times10^6$ Dalton.

If desired, the HA may be a mixture of LMW HA and HMW HA. Reference to the Polymer, LMW HA, HMW HA, and polyamino acid will also include the corresponding alkali metal or alkaline earth metal salts including but not limited to sodium, potassium, and the like. Suitable Polymers include:

(a) Water Absorbing Acrylic or Methacrylic Resins

One suitable polymer is a water-absorbing polymer as disclosed in U.S. Patent Application Publication No. 2016-0030328. This polymer may be obtained from the polymerization of monomers (A), (B) and (C):

Component (A) is a phosphate-containing acrylic or methacrylic monomer. As long as a monomer has a phosphate group and an acrylic or methacrylic group, the structure of a linkage for connecting these two groups is not particularly limited. Exemplary linkages include alkylene groups such as methylene, ethylene and propylene and oxyalkylene groups such as oxyethylene, oxypropylene, oxybutylene, oxypentamethylene and mixtures thereof. Of these, polyoxyalkylene groups are preferred, with polyoxypropylene being most preferred. The monomer is commercially available, for example, under the tradename of Sipomer PAM-200 from Rhodia.

Also included is a salt of a phosphate-containing acrylic or methacrylic monomer, which may be formed by adding an alkaline aqueous solution to the phosphate-containing acrylic or methacrylic monomer.

Component (B) is a monomer having one acrylic or methacrylic group within the molecule other than component (A). Suitable monomers include acrylic acid, methacrylic acid, maleic acid, maleic anhydride, fumaric acid, crotonic acid, itaconic acid, 2-(meth)acrylamide-2-methylpropanesulfonic acid, (meth)acryloxyalkanesulfonic acid, N-vinyl-2-pyrrolidone, N-vinylacetamide, (meth)acrylamide, N-isopropyl(meth)acrylate, N,N-dimethyl(meth)acrylamide, 2-hydroxyethyl(meth)acrylate, methoxypolyethylene glycol(meth)acrylate, polyethylene glycol(meth)acrylate, and stearyl acrylate. A salt of the monomer may be formed by adding an alkaline aqueous solution to the (meth)acrylic monomer.

The "salt" includes alkali metal salts such as sodium, potassium and lithium, alkaline earth metal salts such as calcium, magnesium and barium, and ammonium salts such as quaternary ammonium and quaternary alkyl ammonium. Inter alia, sodium salt is the most common and preferred. Neutralization treatment is preferably carried out at a temperature of 10 to 100° C., more preferably 20 to 90° C. Acrylic acid or polyacrylic acid following polymerization may be neutralized with a base. Neutralization prior to polymerization is preferred because it is time consuming to post-neutralize non-neutralized or low-neutralized (specifically a degree of neutralization of less than 30 mol %) polyacrylic acid following polymerization. The water-absorbing polymer of the invention preferably has a degree of neutralization of 0.01 to 100%, more preferably 1 to 90%, and even more preferably 20 to 80% based on the moles of acid groups in the polymer.

Component (C) is an organopolysiloxane having a (meth)acrylic group at both ends, represented by the general formula (1):

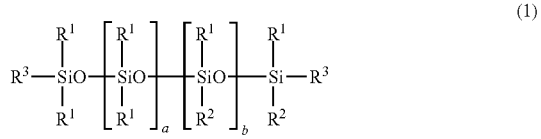

wherein $R^1$ is each independently an aliphatic unsaturation-free monovalent hydrocarbon group having 1 to 8 carbon atoms. $R^2$ is a group containing a polyoxyalkylene group having the general formula (2):

$$—R^4(OC_2H_4)x(OC_3H_6)yOH \quad (2)$$

wherein $R^4$ is each independently a divalent organic group having 2 to 15 carbon atoms, x and y each are an integer of 0 to 30, meeting 1≤x+y≤50, $R^3$ is a substituent group having a (meth)acrylic group, a is an integer inclusive of 0 and b is an integer of at least 1.

Examples of the monovalent hydrocarbon group represented by $R^1$ include alkyl groups such as methyl, ethyl and butyl, cycloalkyl groups such as cyclopentyl and cyclohexyl, aryl groups such as phenyl and tolyl, and aralkyl groups such as benzyl and phenethyl. Inter alia, alkyl groups of 1 to 4 carbon atoms and phenyl are preferred, with methyl being most preferred.

In formula (2), $R^4$ is each independently selected from divalent organic groups having 2 to 15 carbon atoms, for example, —(CH$_2$)$_2$—, —(CH$_2$)$_3$—, —(CH$_2$)$_4$—, —CH$_2$CH(CH$_3$)CH$_2$—, —(CH$_2$)$_8$—, and —(CH$_2$)$_{11}$—. Inter alia, —(CH$_2$)$_2$—, —(CH$_2$)$_3$—, and —(CH$_2$)$_4$— are preferred. Each of x and y is an integer of 0 to 30, meeting 1≤x+y≤50. Preferably each of x and y is an integer of 5 to 25, more preferably 10 to 20, and the sum of x+y is 10 to 45, more preferably 20 to 40.

A preferred suitable water-absorbing polymer is Sodium Polyacrylate Crosspolymer-1, which is a crosslinked polymer that is obtained by the polymerization of methacrylic acid and methacryloyl PPG-6 phosphate and a silicone copolymer prepared by reacting a methacrylate-terminated polydimethylsiloxane polymer containing silicon hydride groups with PEG-18/PPG-17 allyl ether.

(b). Copolymers of Acryloyldimethyltaurate

Also suitable is a thickening polymer obtained from the polymerization of partially salified or completely salified 2-methyl 2-[(1-oxo 2-propenyl) amino] 1-propanesulfonic acid, with at least one neutral monomer selected from acrylamide, (2-hydroxy-ethyl) acrylate or N,N-dimethyl acrylamide, and at least one monomer of formula (I):

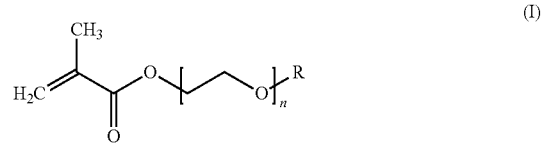

in which R represents a linear or branched alkyl radical having from eight to twenty carbon atoms and n represents a number greater than or equal to one and less than or equal to twenty, selected from tetraethoxylated lauryl methacrylate or eicosaethoxylated stearyl methacrylate in the presence of at one crosslinking agent. This polymer is set forth in U.S. Patent Application Publication No. 2012/0172457 also hereby incorporated by reference in its entirety.

One preferred suitable thickening polymer is a copolymer of ammonium acryloyldialkyltaurate, dialkylacrylamide, lauryl methacrylate and laureth-4 methacrylate, crosslinked with trimethylolpropane triacrylate.

Most preferred is a polymer having the INCI name Polyacrylate Crosspolymer-6 that may be purchased from Seppic Inc under the tradename SepiMAX Zen. Polyacrylate crosspolymer-6 is a copolymer of ammonium acryloyldimethyltaurate, dimethylacrylamide, lauryl methacrylate and laureth-4 methacrylate, crosslinked with trimethylolpropane triacrylate.

(c). Acrylate Crosslinked Silicone Copolymers

Also suitable are acrylate crosslinked silicone copolymers that contain at least one polyether substituted structure unit and at least one epoxy or oxirane structural unit reacted with acrylates to produce crosslinked silicones containing polyether substituted structural networks and acrylate crosslinks. Such polymers are disclosed in U.S. Pat. Nos. 7,687,574 and 7,833,541 which are hereby incorporated by reference in the entirety.

In particular, the polymer may be the reaction product of:

1) $M_a M^H{}_{b-h-k} M^{PE}{}_h M^E{}_k D_c D^H{}_{d-i-l} D^{PE}{}_i D^E{}_l T_e T^H{}_{f-j-m} T^{PE}{}_j T^E{}_m Q_g$ and 2) a stoichiometric or super-stoichiometric quantity of acrylate where $M=R^1 R^2 R^3 SiO_{1/2}$;
$M^H=R^4 R^5 HSiO_{1/2}$;
$M^{PE}=R^4 R^5(-CH_2CH(R^9)(R^{10})_n O(R^{11})_o (C_2H_4O)_p (C_3H_6O)_q (C_4H_8O)_r R^{12}) SiO_{1/2}$;
$M^E=R^4 R^5(-R^{17}R^{18}C-CR^{16}Q_s Q_t R^{15}(COC)R^{13}R^{14}) SiO_{1/2}$
$D=R^6 R^7 SiO_{2/2}$; and
$D^H=R^8 HSiO_{2/2}$
$D^{PE}=R^8(-CH_2CH(R^9)(R^{10})_n O(R^{11})_o (C_2H_4O)_p (C_3H_6O)_q (C_4H_8O)_r R^{12}) SiO_{2/2}$
$D^E=R^8(-R^{17}R^{18}C-CR^{16}Q_s Q_t R^{15}(COC)R^{13}R^{14}) SiO_{2/2}$.
$T=R^{19}SiO_{3/2}$;
$T^H=HSiO_{3/2}$;
$T^{PE}=(-CH_2CH(R^9)(R^{10})_n O(R^{11})_o (C_2H_4O)_p (C_3H_6O)_q (C_4H_8O)_r R^{12}) SiO_{3/2}$;
$T^E=(-R^{17}R^{18}C-CR^{16}Q_s Q_t R^{15}(COC)R^{13}R^{14}) SiO_{3/2}$;
and
$Q=SiO_{4/2}$;

where $R^1$, $R^2$, $R^3 R^4$, $R^5$, $R^6$, $R^7$, $R^8$ and $R^{19}$ are each independently selected from the group of monovalent hydrocarbon radicals having from 1 to 60 carbon atoms;

$R^9$ is H or a 1 to 6 carbon atom alkyl group; $R^{10}$ is a divalent alkyl radical of 1 to 6 carbons;

$R^{11}$ is selected from the group of divalent radicals consisting of $-C_2H_4O-$, $-C_3H_6O-$, and $-C_4H_8O-$; $R^{12}$ is H, a monofunctional hydrocarbon radical of 1 to 6 carbons, or acetyl; $R^{13}$, $R^{14}$, $R^{15}$, $R^{16}$, $R^{17}$ and $R^{18}$ are each independently selected from the group of hydrogen and monovalent hydrocarbon radicals having from one to sixty carbon atoms, $Q_t$ is a di- or trivalent hydrocarbon radical having from one to sixty carbon atoms, $Q^5$ is a divalent hydrocarbon radical having from one to sixty carbon atoms subject to the limitation that when $Q_t$ is trivalent $R^{14}$ is absent and $R^{16}$ and $R^{18}$ may be either cis- or trans- to each other;

the subscript a may be zero or positive subject to the limitation that when the subscript a is zero, b must be positive;

the subscript b may be zero or positive subject to the limitation that when b is zero, the subscript a must be positive;

the subscript c is positive and has a value ranging from about 5 to about 1,000;

the subscript d is positive and has a value ranging from about 3 to about 400;

the subscript e is zero or positive and has a value ranging from 0 to about 50;

the subscript f is zero or positive and has a value ranging from 0 to about 30;

the subscript g is zero or positive and has a value ranging from 0 to about 20;

the subscript h is zero or positive and has a value ranging from 0 to about 2 subject to the limitation that the sum of the subscripts h, i and j is positive;

the subscript i is zero or positive and has a value ranging from 0 to about 200 subject to the limitation that the sum of the subscripts h, i and j is positive;

the subscript j is zero or positive and has a value ranging from 0 to about 30 subject to the limitation that the sum of the subscripts h, i and j is positive;

the subscript k is zero or positive and has a value ranging from 0 to about 2 subject to the limitation that the sum of the subscripts k, l and m is positive;

the subscript l is zero or positive and has a value ranging from 0 to about 200 subject to the limitation that the sum of the subscripts k, l and m is positive;

the subscript m is zero or positive and has a value ranging from 0 to about 30 subject to the limitation that the sum of the subscripts k, l and m is positive;

the subscript n is zero or one;

the subscript o is zero or one;

the subscript p is zero or positive and has a value ranging from 0 to about 100 subject to the limitation that (p+q+r)>0;

the subscript q is zero or positive and has a value ranging from 0 to about 100 subject to the limitation that (p+q+r)>0;

the subscript r is zero or positive and has a value ranging from 0 to about 100 subject to the limitation that (p+q+r)>0;

the subscript s is zero or one;

the subscript t is zero or one; and 3) a free radical initiator.

A preferred suitable polymer is Polyacrylate Crosspolymer-7, which is a copolymer of methacrylate PPG-6 phosphate and one or more monomers of acrylic acid, methacrylic acid or one of their simple esters, crosslinked with dimethicone PEG/PPG-25/29 acrylate.

(d). Anionic Polysaccharides

Also suitable are one or more naturally derived anionic polysaccharides including alginic acid or its sodium salt.

A more preferred suitable natural anionic polysaccharide is sodium alginate.

The treatment composition should also contain the ingredient used to test the polymer for formation of the micromesh structure. In the case where the glycosaminoglycan was hyaluronic acid (HA), it may vary in molecular weight or be a mixture of low and high molecular weight HAs.

The treatment composition may be in a variety of forms including an emulsion, either water in oil or oil in water emulsion. If in the form of an emulsion, the composition may contain from about 1-99%, preferably from about 5-90%, more preferably from about 10-85% water and from about 1-99%, preferably from about 5-90%, more preferably from about 5-75% of oil. If in the form of an aqueous suspension or dispersion, the composition may generally contain from about 1-99.9%, preferably from about 5-95%, more preferably from about 10-90% water, with the remaining ingredients being the active ingredients or other formula ingredients.

2. The Glycosamnoglycan

Whatever glycosaminoglycan is used to establish that the polymer forms the micro-mesh must also be formulated into the treatment composition. In the case where the glycosaminoglycan is HA then that HA will be incorporated into the treatment composition. In one particularly preferred form, the HAs are a mixture of low and high molecular weights (LMW HA and HMW HA) cosmetic composition comprises at least one LMW HA and at least one HMW HA.

Preferably the weight ratio of LMA HA to HMW HA may range from about 100:1 to 1:100, preferably about 50:1 to 1:50, more preferably about 15:1 to 1:15.

(a). High Molecular Weight Hyaluronic Acid

The HMW HA has a molecular weight ranging from about $8 \times 10^5$ Dalton to $1 \times 10^7$ Dalton, preferably from $1 \times 10^6$ Dalton to $8 \times 10^6$ Dalton, more preferably from $1.2 \times 10^6$ Dalton to $3 \times 10^6$ Dalton. The HMW HA may be synthetic or it may be obtained by biotechnological processing by fermenting yeasts such as saccharomyces in fermentation processes. A suitable HMW HA for use in the claimed composition may be purchased from Contipro Biotech s.r.o. under the name Hyaluronic Acid, Sodium Salt which has the INCI name Sodium Hyaluronate.

Suggested ranges of HMW HA may range from about 0.001 to 10%, preferably about 0.005 to 5% and more preferably about 0.01 to 1.5% by weight of the total composition.

(b). Low Molecular Weight Hyaluronic Acids (LMW HA)

The molecular weight of the LMA HA or its salt may range from about $1 \times 10^3$ Dalton to $8 \times 10^5$ Dalton, preferably from $5 \times 10^3$ Dalton to $1 \times 10^5$ Dalton, more preferably from $8 \times 10^3$ Dalton to $5 \times 10^4$ Dalton. The LMW HA may also be synthetic or it may be obtained by biotechnological processing by fermenting yeasts such as saccharomyces from fermentation processes. A suitable hyaluronic acid for use in the claimed composition may be purchased from Contipro Biotech s.r.o. under the name HyActive powder which has the INCI name Sodium Hyaluronate.

Suggested ranges of LMW HA range from about 0.001 to 10%, preferably about 0.005 to 5% and more preferably about 0.01 to 1.5% by weight of the total composition.

3. Other Ingredients

The treatment composition may contain other ingredients including but not limited to those set forth herein A. Autophagy Activator One optional ingredient present in the treatment composition is an autophagy activator, which, if present, may be in amounts ranging from about 0.00001 to 20%, preferably 0.0001-5%, more preferably from about 0.001 to 1%.

Examples of ingredients that are known to stimulate autophagy are yeast extracts including but not limited to those from the genuses such as *Lithothamnium, Melilot, Citrus, Candida, Lens, Urtica, Carambola, Momordica, Yarrowia, Plumbago*, etc. Further specific examples include *Lithothamniumn calcaneum, Melilotus officinalis, Citrus limonum, Candida saitoana, Lens culinaria, Urtica dioica, Averrhoa carambola, Momordica charantia, Yarrowia lipolytica, Plumbago zeylanica* and so on.

B. Proteasome Activator

Another optional ingredient in the treatment composition is a proteasome activator which, if present, may range from about 0.0001 to 5%, preferably from about 0.0005 to 2.0%, more preferably from about 0.001 to 1.5%.

Suitable proteasome activators are any compounds, molecules, or active ingredients that stimulate proteasome activity in the cells of keratin surfaces.

Examples of suitable proteasome activators include, but are not limited to, algin, alginates, hydrolyzed algin, molasses extract, *Trametes* extracts, including extracts from *Trametes versicolor*, olea hydroxol.

C. CLOCK, PER1 Gene Activator

Another optional ingredient in the treatment composition is a CLOCK or PER1 cellular gene activator. Suggested ranges are from about 0.000001 to about 3.0%, preferably from about 0.000005 to 2.5%, more preferably from about 0.00001 to 2%. Suitable CLOCK or PER1 activators may be present in the form of botanical extracts, polypeptides, peptides, amino acids, and the like.

1. Peptide CLOCK or PER1 Gene Activator

A particularly preferred CLOCK and/or PER1 gene activator comprises a peptide of the formula (I):

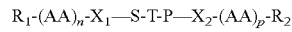

where $(AA)_n$-$X_1$—S-T-P—$X_2$-$(AA)_p$ is (SEQ ID No. 1), and:

$X_1$ represents a threonine, a serine, or is equal to zero, $X_2$ represents an isoleucine, leucine, proline, valine, alanine, glycine, or is equal to zero, AA represents any amino acid or derivative thereof, and n and p are whole numbers between 0 and 4, $R_1$ represents the primary amine function of the N-terminal amino acid, either free or substituted by a protective grouping that may be chosen from either an acetyl group, a benzoyl group, a tosyl group, or a benzyloxycarbonyl group, R2 represents the hydroxyl group of the carboxyl function of the C-terminal amino acid, substituted by a protective grouping that may be chosen from either a C1 to C20 alkyl chain or an NH2, NHY, or NYY group with Y representing a C1 to C4 alkyl chain, wherein the sequence of general formula (I) comprises from about 3 to 13 amino acid residues, said sequence of general formula (I) possibly containing substitutions of amino acids $X_1$ and $X_2$ with other chemically equivalent amino acids; wherein the amino acids are: Alanine (A), Arginine (R), Asparagine (N), Aspartic Acid (D), Cysteine (C), Glutamic Acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y), Valine (V). More preferred, are peptides of the above formula, as follows:

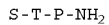

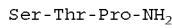

(SEQ ID No. 2)

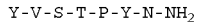

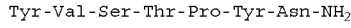

(SEQ ID NO. 3)

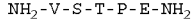

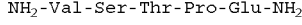

(SEQ ID No. 4)

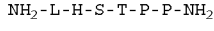

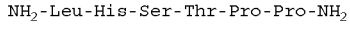

(SEQ ID No. 5)

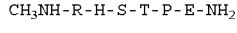

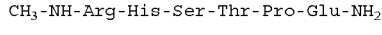

(SEQ ID No. 6)

especially S-T-P—$NH_2$, or $NH_2$-L-H—S-T-P—P—$NH_2$ (SEQ ID No. 4), or mixtures thereof. S-T-P—NH2 is available from ISP-Vinscience under the trademark Chronolux® and having the INCI name Tripeptide-32. Also highly preferred is S-P-L-Q-NH₂ (SEQ ID No. 7)

Ser-Pro-Leu-Gln-NH₂ a peptide manufactured by ISP-Vinscience under the trademark Chronogen® and having the INCI name Tetrapeptide-26.

2. Botanical Extracts

Also suitable as the CLOCK or PER1 gene activator is cichoric acid or isomers or derivatives thereof. Cichoric acid may be synthetic or naturally derived. Synthetic cichoric acid may be purchased from a number of commercial manufacturers including Sigma Aldrich. Cichoric acid may also be extracted from botanical sources that are known to contain cichoric acid such as *Echinacea, Cichorium, Taraxacum, Ocimum, Melissa*, or from algae or sea grasses. More specifically, botanical extracts such as *Echinacea purpurea, Cichorium intybus, Taraxacum officinale, Ocimum basilicum*, or *Melissa officinalis*. The term "cichoric acid" when used herein also includes any isomers thereof that are operable to increase PER1 gene expression in skin cells.

A specific example includes a botanical extract from *Echinacea purpurea* sold by Symrise under the brand name Symfinity™ 1298 which is a water extract of *Echinacea purpurea* which is standardized during the extraction process to contain about 3% by weight of the total extract composition of cichoric acid. *Echinacea* extracts from different sources will vary in cichoric acid content, and as such will yield variable results in induction of PER1 gene expression. Ethanolic extract of the roots of *Echinacea* purpura will provide more cichoric acid than ethanolic extracts of *Echineacea angustifolia* or *Echinacea pallida*. The content of active ingredients in any extract is also very dependent on the method of extraction. For example, it is known that in many cases enzymatic browning during the extraction process will reduce the phenolic acid content of the resulting extract.

D. DNA Repair Enzymes

Another optional ingredient in the treatment composition is a DNA repair enzyme. Suggested ranges are from about 0.00001 to about 5%, preferably from about 0.00005 to about 3%, more preferably from about 0.0001 to about 2.5% of one or more DNA repair enzymes.

One example of such a DNA repair enzyme may be purchased from AGI/Dermatics under the trade name Roxisomes®, and has the INCI name *Arabidopsis Thaliana* extract. It may be present alone or in admixture with lecithin and water. This DNA repair enzyme is known to be effective in repairing 8-oxo-Guanine base damage.

Another type of DNA repair enzyme that may be used is one that is known to be effective in repairing 06-methyl guanine base damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of *Micrococcus* lysate (an end product of the controlled lysis of various species of *micrococcus*), lecithin, and water. Photosomes® comprise a mixture of plankton extract (which is the extract of marine biomass which includes one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as *Bifida* lysate or *Bifida* ferment lysate, the latter a lysate from *Bifido* bacteria which contains the metabolic products and cytoplasmic fractions when *Bifido* bacteria are cultured, inactivated and then disintegrated. This material has the INCI name *Bifida* Ferment Lysate.

E. Humectants

The composition may contain one or more humectants. If present, they may range from about 0.01 to 35%, preferably from about 0.5 to 20%, more preferably from about 0.5 to 15%. Examples of suitable humectants include glycols, sugars, and the like. Suitable glycols are in monomeric or polymeric form and include polyethylene and polypropylene glycols such as PEG 4-10, which are polyethylene glycols having from 4 to 10 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

F. Surfactants

It may be desirable for the composition to contain one more surfactants, especially if in the emulsion form. However, such surfactants may be used if the compositions are solutions, suspensions, or anhydrous also, and will assist in dispersing ingredients that have polarity, for example pigments. Such surfactants may be silicone or organic based. The surfactants will also aid in the formation of stable emulsions of either the water-in-oil or oil-in-water form. If present, the surfactant may range from about 0.001 to 10%, preferably from about 0.005 to 8%, more preferably from about 0.1 to 5% by weight of the total composition.

1. Organic Nonionic Surfactants

The composition may comprise one or more nonionic organic surfactants. Suitable nonionic surfactants include alkoxylated alcohols or ethers, formed by the reaction of an alcohol with an alkylene oxide, usually ethylene or propylene oxide. Suitable alcohols include mono-, di-, or polyhydric short chain (C1-6) alcohols; aromatic or aliphatic saturated or unsaturated fatty (C12-40) alcohols, of cholesterol; and so on.

In one embodiment the alcohol is cholesterol, or an aromatic or aliphatic saturated or unsaturated fatty alcohol which may have from 6 to 40, preferably from about 10 to 30, more preferably from about 12 to 22 carbon atoms. Examples include oleyl alcohol, cetearyl alcohol, cetyl alcohol, stearyl alcohol, isostearyl alcohol, behenyl alcohol, and the like. Examples of such ingredients include Oleth 2-100; Steareth 2-100; Beheneth 5-30; Ceteareth 2-100; Ceteth 2-100; Choleth 2-100 wherein the number range means the number of repeating ethylene oxide units, e.g. Ceteth 2-100 means Ceteth where the number of repeating ethylene oxide units ranges from 2 to 100. Derivatives of alkoxylated alcohols are also suitable, such as phosphoric acid esters thereof.

Some preferred organic nonionic surfactants include Oleth-3, Oleth-5, Oleth-3 phosphate, Choleth-24; Ceteth-24; and so on.

Also suitable are alkoxylated alcohols formed with mono-, di-, or polyhydric short chain alcohols, for example those having from about 1 to 6 carbon atoms. Examples include glucose, glycerin, or alkylated derivatives thereof. Examples include glycereth 2-100; gluceth 2-100; methyl gluceth 2-100 and so on. More preferred are methyl gluceth-20; glycereth-26 and the like.

Other types of alkoxylated alcohols are suitable surfactants, including ethylene oxide polymers having varying numbers of repeating EO groups, generally referred to as PEG 12 to 200. More preferred are PEG-75, which is may be purchased from Dow Chemical under the trade name Carbowax PEG-3350.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

2. Silicone or Silane Surfactants

Also suitable are various types of silicone or silane-based surfactants. Examples include organosiloxanes substituted with ethylene oxide or propylene oxide groups such as PEG dimethicones which are dimethicones substituted with polyethylene glycols including those having the INCI names PEG-1 dimethicone; PEG-4 dimethicone; PEG-8 dimethicone; PEG-12 dimethicone; PEG-20 dimethicone; and so on.

Also suitable are silanes substituted with ethoxy groups or propoxy groups or both, such as various types of PEG methyl ether silanes such as bis-PEG-18 methyl ether dimethyl silane; and so on.

Further examples of silicone based surfactants include those having the generic names dimethicone copolyol; cetyl dimethicone copolyol; and so on.

G. Oils

In the event the compositions of the invention are in emulsion form, the composition will comprise an oil phase. Oily ingredients are desirable for the skin moisturizing and protective properties. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C. If present, such oils may range from about 0.01 to 85%, preferably from about 0.05 to 80%, more preferably from about 0.1 to 50%.

The oils may include volatile silicones or volatile paraffinic hydrocarbons, or non-volatile silicones or organic oils.

Examples include monoesters including hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on; diesters such as diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on; or triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

K. Preferred Compositions

Examples of preferred embodiments for the treatment composition having microscopic three dimensional spherical structures that may be incorporated into the package include one or more of the below:

An oil in water emulsion comprising 10-95% water, 0.1 to 5% of the Polymer, from 0.1 to 10% of the glycosaminoglycan, 0.1 to 10% nonionic surfactant, 0.1-5% humectant, and at least one OGG1 DNA repair enzyme.

An oil in water emulsion comprising 10-95% water, 0.1 to 5% of the Polymer, from 0.1 to 10% of the glycosaminoglycan, 0.1 to 10% nonionic surfactant, 0.1-5% humectant, and from 0.001-5% of an autophagy activator.

An oil in water emulsion comprising 10-95% water, 0.1 to 5% of the Polymer, from 0.1 to 10% of the glycosaminoglycan, 0.1 to 10% nonionic surfactant, 0.1-5% humectant, and from 0.005-2% of at least one proteasome activator.

An oil in water emulsion comprising 10-95% water, 0.1 to 5% of the Polymer, from 0.1 to 10% of the glycosaminoglycan, 0.1 to 10% nonionic surfactant, 0.1-5% humectant, and from 0.00001-2% of at least one CLOCK or PER1 gene activator.

An oil in water emulsion comprising 5-99% water, 0.01 to 5% of a polymer selected from the group consisting of Polyacrylate crosspolymer-6, Sodium polyacrylate crosspolymer-1, Polyacrylate crosspolymer-7, alginic acid or the sodium salt; from 0.01 to 15% of hyaluronic acid, and water.

The invention will be further described in connection with the following examples which are set forth for the purposes of illustration only.

Example 1

Micro-mesh compositions were prepared as follows:

| Ingredient | | Concentration |
|---|---|---|
| Trade Name | INCI Name | (Wt %) |
| Sepimax Zen | Polyacrylate Crosspolymer-6 | 0.1 |
| Hyaluronic Acid, Sodium Salt | Sodium Hyaluronate (HMW) | 0.11 |
| Hyactive 10 | Sodium Hyaluronate (LMW) | 0.05 |
| Aquadew SPA-30B | Sodium Polyaspartate | 0.5 |
| Phenoxyethanol | Phenoxyethanol | 0.5 |
| | Water | q.s. 100 |

The composition was prepared by combining phenoxyethanol and water and mixing well. Hyaluronic acid in the form of a mixture of low and high molecular weight hyaluronic acids was added to the mixture until uniform. Polyacrylate crosspolymer-6 was then added and mixed well till uniform. Sodium polyaspartate was added last and the mixture mixed well till uniform.

Figure 6:
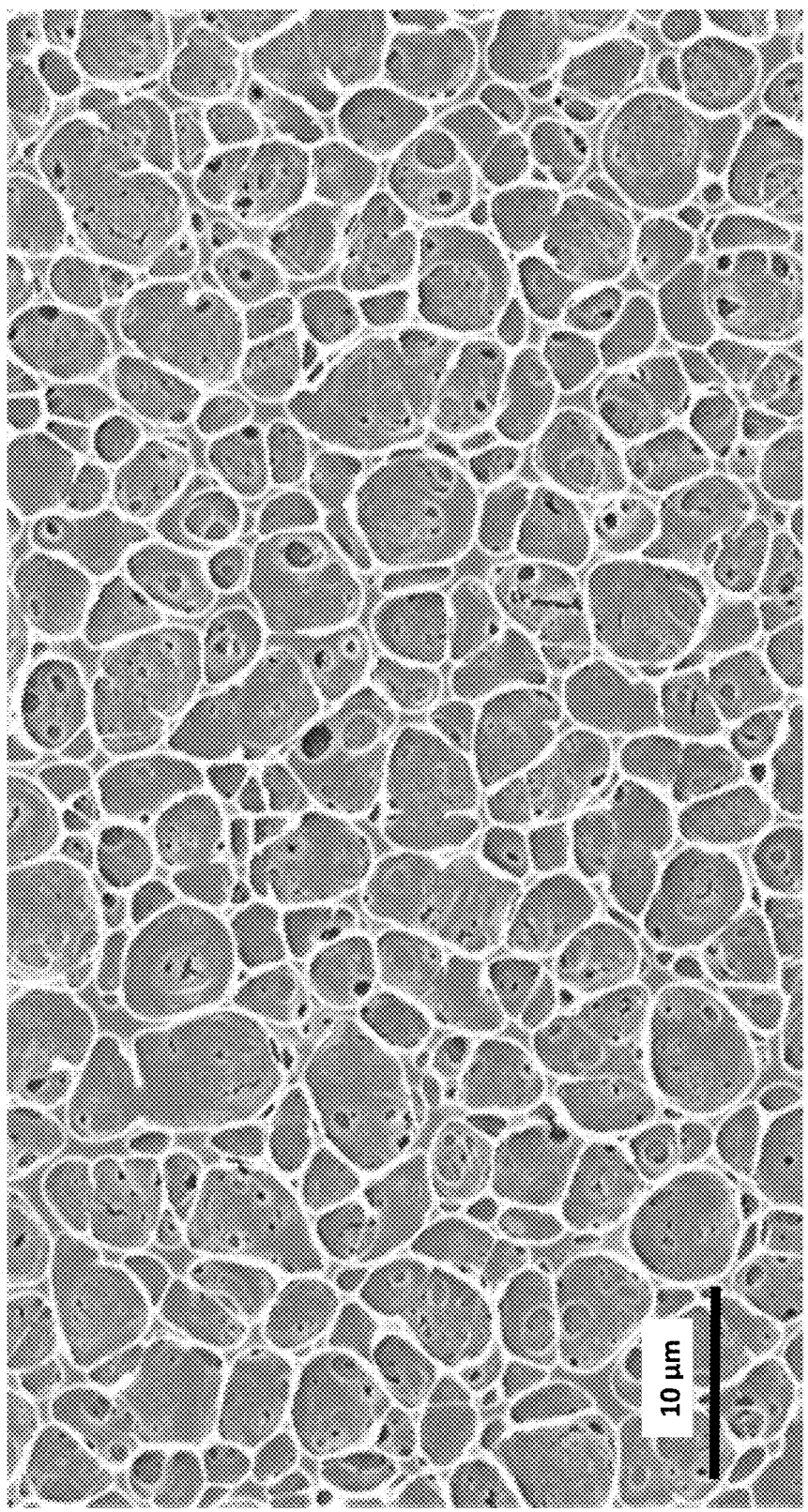
FIG. 6 shows the spherical structures having membranous outer walls and secluded inner spaces.

The composition was scanned with a Zeiss SEM. The SEM image on FIG. 6 was a view of the micro-mesh structure with the scale bars shown at the bottom left corner of each image.

Example 2

Skincare compositions were made as following:

| Ingredient | | Concentration (Wt %) | |
|---|---|---|---|
| Trade Name | INCI Name | #1 | #2 |
| Sepixmax Zen | Polyacrylate Crosspolymer-6 | 0 | 0.1 |
| Hyaluronic Acid, Sodium Salt | Sodium Hyaluronate | 0 | 0.11 |
| Hyactive 10 | Sodium Hyaluronate | 0 | 0.05 |
| Aquadew SPA-30B | Sodium Polyaspartate | 0.5 | 0.5 |
| Purified Water | Water | 36.4 | 36.1 |
| Bifidus Extract Cl Pk Ehg | Water\Aqua\Eau/Bifida Ferment Lysate/Ethylhexylglycerin | 9.4 | 9.4 |
| Bentone Gel Ihd V | Isohexadecane/Disteardimonium Hectorite/Propylene Carbonate | 7.5 | 7.5 |
| Xiameter Pmx-200 Silicone Fl. 5cs | Dimethicone | 7 | 7 |
| Net Ws-Cf | Dimethicone/Peg-10 Dimethicone/Disteardimonium Hectorite | 6.25 | 6.25 |
| Glycerine Usp 99% (Vegetable) | Glycerin | 6 | 6 |
| Gransil Dm5 | Dimethicone/Polysilicone-11 | 5 | 5 |
| 1,3 Butylene Glycol | Butylene Glycol | 3 | 3 |
| Bifisomes Pk Ehg | Water\Aqua\Eau/Bifida Ferment Lysate/Hydrogenated Lecithin | 3 | 3 |
| Dow Corning 2501 Cosmetic Wax | Bis-Peg-18 Methyl Ether Dimethyl Silane | 3 | 3 |
| Hydrovance Moisturizing Agent | Hydroxyethyl Urea | 2 | 2 |
| Sp Arlamol Ps15e-Mbal-Lq-(Ap) | Ppg-15 Stearyl Ether | 1 | 1 |
| Wickenol 131 | Isopropyl Isostearate | 1 | 1 |
| Sucrose, Ultra Pure | Sucrose | 1 | 1 |
| Phytofix | Propylene Glycol Dicaprate/*Helianthus Annus* (Sunflower) Seed Cake/*Hordeum Vulgare* (Barley) Extract/*Cucumis Sativus* (Cucumber) Fruit Extract | 1 | 1 |
| Tixogel Idp 1388 | Isododecane/Polyethylene | 1 | 1 |
| Trehalose Kama | Trehalose | 1 | 1 |
| Hydrolite 5, 2/016020 | Pentylene Glycol | 1 | 1 |
| Polysea Pf | Algae Extract | 0.75 | 0.75 |
| Phenoxetol | Phenoxyethanol | 0.6 | 0.6 |
| Biphyderm Jk | *Glycine Soya* (Soybean) Extract/Bifida Ferment Lysate | 0.5 | 0.5 |
| Silicone Hl88 | Dimethicone | 0.5 | 0.5 |
| Vitamin E, Usp, Fcc, Code 0420085 | Tocopheryl Acetate | 0.5 | 0.5 |
| Caffeine Powder | Caffeine | 0.2 | 0.2 |
| Chronolux ® | Water\Aqua\Eau/Butylene Glycol/Tripeptide-32 | 0.2 | 0.2 |
| Sorbitol Solution 70% | Sorbitol | 0.1 | 0.1 |
| Catacell | Yeast Extract | 0.1 | 0.1 |
| *Camelina* Oil | *Camelina Sativa* Seed Oil | 0.1 | 0.1 |
| BHT | BHT | 0.09 | 0.09 |
| Viapure *Poria* | *Poria Cocos* Extract | 0.05 | 0.05 |
| Tristat Sdha | Sodium Dehydroacetate | 0.05 | 0.05 |

-continued

| Ingredient | | Concentration (Wt %) | |
|---|---|---|---|
| Trade Name | INCI Name | #1 | #2 |
| EDETA Bd/Na2 | Disodium EDTA | 0.05 | 0.05 |
| Roxisomes O | Water\Aqua\Eau/Yeast Extract/Lecithin | 0.05 | 0.05 |
| Adasomes | *Lactobacillus* Ferment/Lecithin/Water\Aqua\Eau | 0.05 | 0.05 |
| Aminopropyl Ascorbyl Phosphate | Aminopropyl Ascorbyl Phosphate | 0.045 | 0.045 |
| Chamomile Romaine Oil 627 | *Anthemis Nobilis* (Chamomile) | 0.015 | 0.015 |
| Silymarin | Lady's Thistle (*Silybum Marianum*) Fruit Extract | 0.015 | 0.015 |
| A00138 Phytoclar Ii Bg Nextgen | Butylene Glycol/*Scutellaria Baicalensis* Root Extract/*Morus Bombycis* Root Extract | 0.01 | 0.01 |
| Phytosphingosine | Phytosphingosine | 0.01 | 0.01 |
| Mangosteen 90% (324880) | *Garcinia Mangostana* Peel Extract | 0.01 | 0.01 |
| Phyko-Ai Pf | Water/Hydrolyzed Algin | 0.005 | 0.005 |
| White Birch Extract Premier | *Betula Alba* (Birch) Extract | 0.001 | 0.001 |
| Pure Oxy Red 1x-34-Pc-3551 | Iron Oxides | 0.0005 | 0.0005 |

Formulas 1 and 2 were prepared. Formula 1 is not in the micro-mesh form because it is missing the mesh-forming polymer, Polyacrylate crosspolymer-6. Formula 2 contains the micro-mesh forming ingredients. A clinical study was performed on fifteen panelists to evaluate the efficacy of formulas 1 and 2 on the thickness of the stratum corneum of the under-eye area. The test areas in this study were the left and the right under-eye area. A split face study was performed where 300 µL of the formulas 1 and 2 were applied on the left and right side of the face. Compositions were applied to the subjects in a left/right randomized way. The stratum corneum was evaluated in the under-eye area at baseline and 4 hours after treatment by Reflectance Confocal Microscopy (RCM). A handheld Vivascope 3000 (Lucid, 1.5x, field of view=0.5×0.5 mm) was used in which the contrast is provided by differences in refractive index (SOP A.18v1, labbook 1846-1 p 99). At least 5 Vivastacks with a minimal optical slice thickness of 1.96 µm were recorded of the different test areas. Aquasonic clear gel was used as immersion fluid between the objective lens and the tissue cap as well as between the tissue cap and the skin. The thickness of the stratum corneum was determined by measuring the difference in depth between the top of the stratum corneum and the top of the stratum granulosum (first layer with visible cells). Data on the different compositions were collected on the same panelist and statistically evaluated with a paired Student's t-test. Differences over time and between treatments were considered as significant if p≤0.05.

The stratum corneum was evaluated with Reflectance Confocal Microscopy (RCM) using the Vivascope 3000. Confocal images were used to determine the thickness of the stratum corneum at baseline and 4 hours after treatment.

Figure 7:
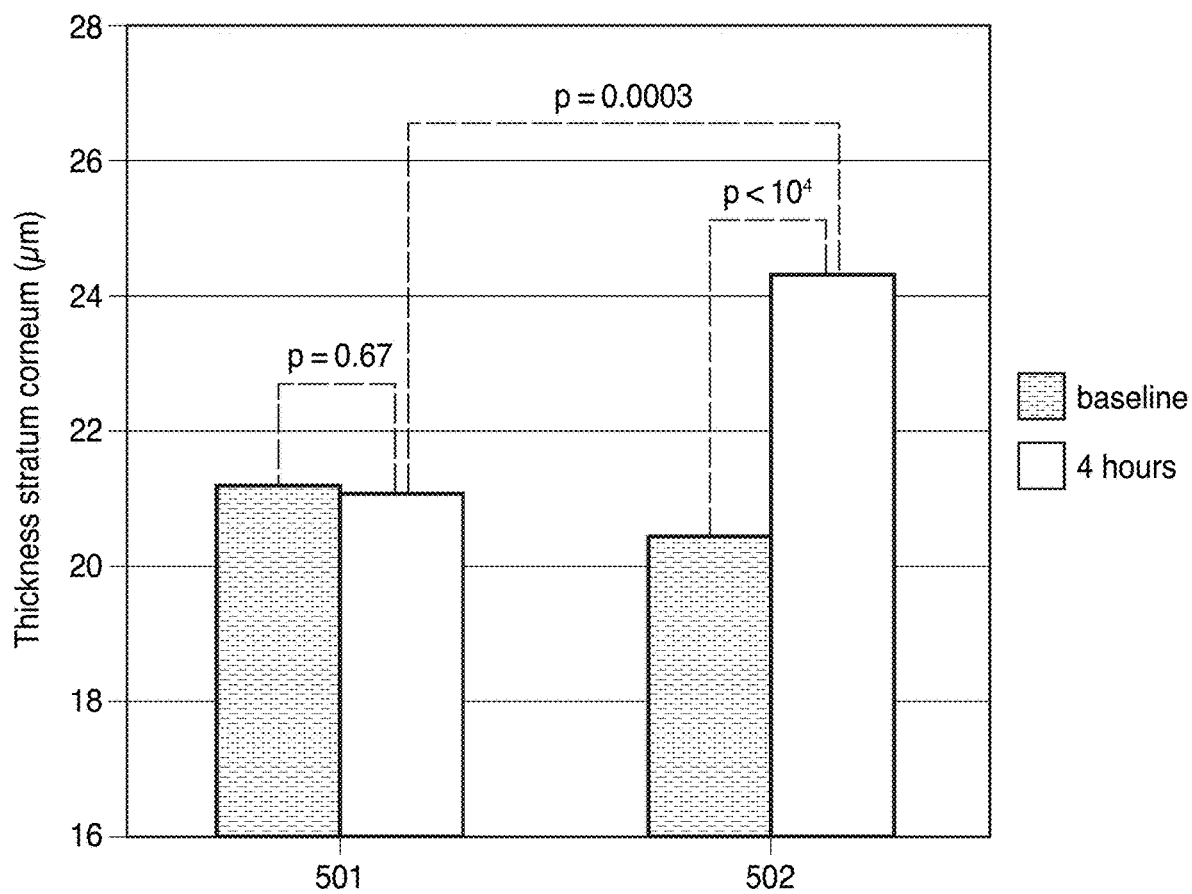
FIG. 7 shows the results of comparative testing of compositions as described in Example 2 demonstrating improvement of stratum corneum thickness when using the packaged composition of the invention.

Four hours after treatment with the composition 2, the stratum corneum thickness increased significantly in the under-eye area compared to baseline (p<10-4)(see FIG. 7). There was a significant difference in stratum corneum thickness between the side treated with composition 1 and 2 (p=0.0003). For composition 1 there was no difference compared to baseline (p=0.67).

Figure 8:
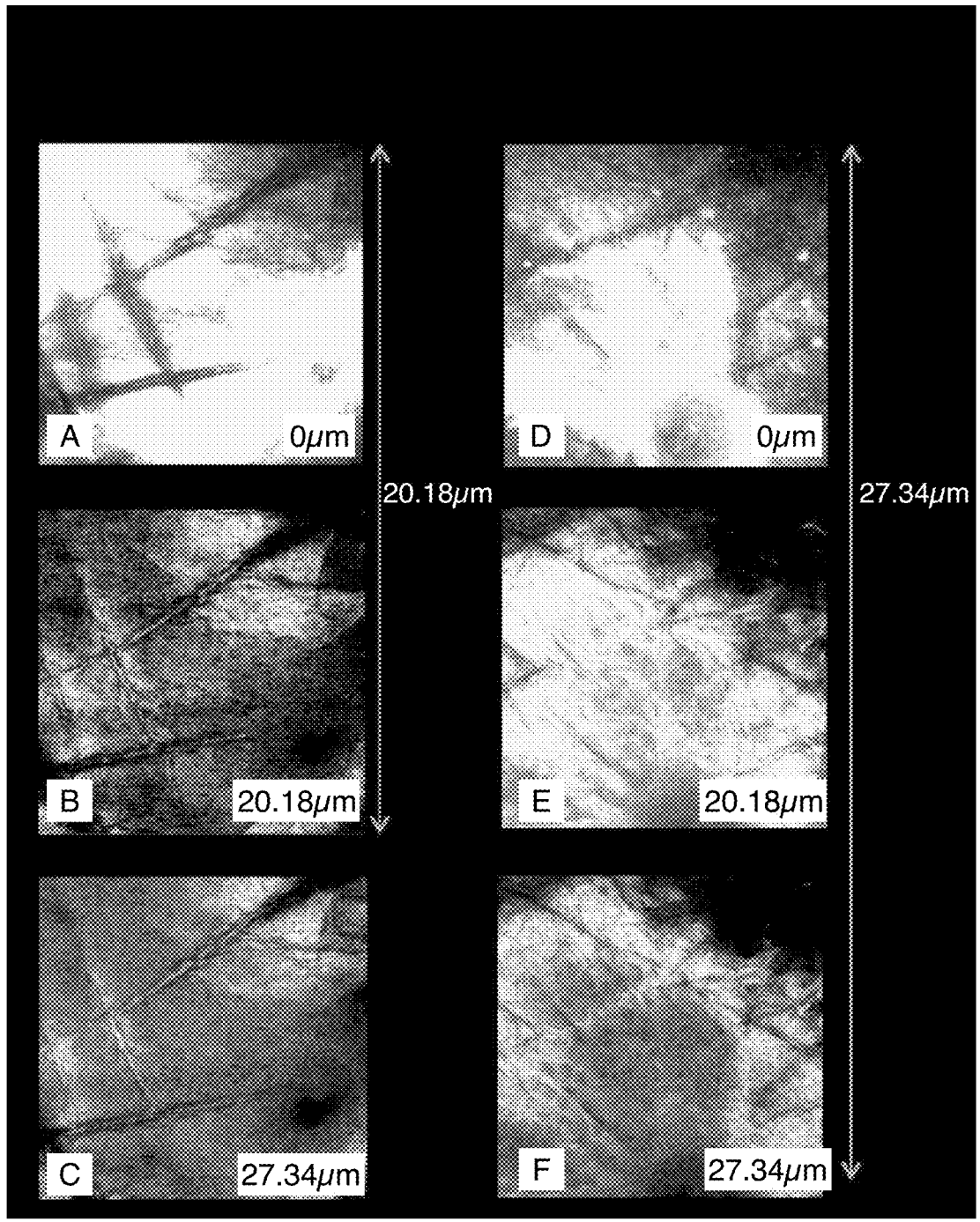
FIG. 8 shows the results of stratum corneum and granulosum penetration of the composition of the invention and a comparative composition taken 4 hours after application.

FIG. 8 shows representative reflectance confocal images of the stratum corneum and the stratum granulosum of the under-eye area of one panelist taken 4 hours after product application. On each image the depth of recording (average of 5 'stacks') is given. On the site treated with the composition 1 (image A, B, C), the stratum granulosum (image B) was detected at 20.18 µm below the top of the stratum corneum (image A). At the site treated with composition 2 (image D, E, F) the stratum granulosum (image F) was detected at 27.34 µm below the top of the stratum corneum (image D). This illustrates the thickening of the stratum corneum on the composition 2 treated site.

This illustrates an instant physical plumping effect of the stratum corneum of the under-eye area by the Micro-Mesh technology particularly when applied in the form of the packaged composition of the invention.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A packaged skin treatment composition comprising:
   (a) a receptacle with a neck and having stored therein a treatment composition containing microscopic three dimensional spherical structures having membranous outer walls and secluded internal spaces,
   (b) a wiper affixed within the neck and having an internal barrel portion,
      wherein said wiper is affixed in said neck with a collar having downwardly extending arms forming a circumferential depression;
      wherein said internal barrel portion is formed by downwardly extending circumferential walls terminating in a distal portion which is an orifice surrounded by a shelf having holes therein;
   (c) a closure for the receptacle,
   (d) an applicator comprised of a rod with a proximal end affixed to the closure and a distal end terminating in an enlarged portion,
wherein when the applicator is extracted from the receptacle the treatment composition loads onto the rod to permit application of the treatment composition containing the microscopic spherical structures to the treatment surface; wherein when the applicator is extracted through the wiper, the sides of said enlarged portion of the applicator is wiped clean of the treatment composition by said shelf surrounding the orifice.

2. The packaged skin treatment composition of claim 1 wherein the treatment surface is around the eye and the treatment composition is an eye treatment composition.

3. The packaged skin treatment composition of claim 1 wherein the receptacle is glass.

4. The packaged skin treatment composition of claim 1 wherein the holes have an external border.

5. The packaged skin treatment composition of claim 1 wherein the holes are evenly spaced along the shelf.

6. The packaged skin treatment composition of claim 1 wherein said proximal end of the rod has a gate.

7. The packaged skin treatment composition of claim 6 wherein the rod has a head and neck and the head and neck extend upwardly from the gate.

8. The packaged skin treatment composition of claim 6 wherein the rod has an enlarged circumferential band.

9. The packaged skin treatment composition of claim 6 wherein the rod has a cross-sectional diameter that ranges from 4.5 to 5.5 millimeters and the enlarged portion has a cross-sectional diameter ranging from 5.6 to 6.6 millimeters.

10. The packaged skin treatment composition of claim 6 wherein the applicator is made of a clear or translucent thermoplastic material selected from polyethylene terephthalate or polyethylene terephthalate glycol.

11. The packaged skin treatment composition of claim 1 wherein the distal orifice of the wiper has a diameter ranging 5.6 to 7.6 mm.

12. The packaged skin treatment composition of claim 1 wherein the closure comprises a cap shell and an inner cap and cap shell fits over inner cap.

13. The packaged skin treatment composition of claim 12 wherein the inner cap has circumferentially downwardly extending ribs that terminate in a bead that extends the circumference of the cap on the upper end thereof.

14. The packaged skin treatment composition of claim 13 wherein inner cap contains a series of panels that extend upwardly from the bead.

15. The packaged skin treatment composition of claim 14 wherein the panels are supported by struts.

16. The packaged skin treatment composition of claim 1 wherein said holes in said shelf do not penetrate through said shelf.

17. A packaged skin treatment composition comprising:
   (a) a receptacle with a neck and having stored therein a treatment composition containing microscopic three dimensional spherical structures having membranous outer walls and secluded internal spaces,
   (b) a wiper having a collar with downwardly projecting arms that form a circumferential depression for seating the wiper within the neck, and an internal barrel portion formed by downwardly extending walls terminating in an orifice surrounded by a shelf having holes surrounded by an external border,
   (c) a closure for the receptacle comprising a cap shell and an inner cap where the inner cap has downwardly extending ribs on the exterior surface thereof, upwardly extending panels, struts, and a central core and the downwardly extending ribs have an upper surface that terminates in a bead the runs the circumference of the cap and the upwardly extending panels extend above the bead and are held in place by the struts which connect the panels to the central core which has top walls and side walls and a hollow interior portion having an extending wall, (d) an applicator comprised of a rod with a proximal end affixed to the extending wall of the hollow interior portion of the central core of the inner cap, and a distal end terminating in an enlarged portion wherein the cross-sectional diameter of the enlarged portion is greater than the cross-sectional diameter of the orifice and the rod, wherein when the applicator is extracted from the receptacle the treatment composition is loaded onto the rod to permit application of the treatment composition containing the microscopic spherical structures to the treatment surface;

wherein when the applicator is extracted through the wiper, the treatment composition is wiped off from the sides of said enlarged portion of the applicator by said shelf surrounding the orifice of the wiper.

18. The packaged treatment composition of claim 17 wherein when the applicator is extracted from the receptacle the treatment composition is loaded onto the rod and the distal tip of enlarged portion to permit application of an amount of treatment composition to a treatment surface that is under the eye and over the eye respectively.

19. A method for applying a treatment composition containing microscopic three dimensional spherical structures having membranous outer walls and secluded internal spaces to the skin comprising the steps of:

Storing the treatment composition in a receptacle with a neck and a wiper affixed within the neck having an internal barrel portion, a closure for the receptacle and an applicator comprised of a rod with a proximal end affixed to the closure and an a distal end terminating in an enlarged portion, wherein said internal barrel portion is formed by downwardly extending circumferential walls terminating in a distal portion which is an orifice surrounded by a shelf having holes therein, Extracting the applicator from the receptacle and loading the treatment composition thereon, wherein when the applicator is extracted through the wiper, the sides of said enlarged portion of the applicator is wiped clean of the treatment composition by said shelf surrounding the orifice, Applying the treatment composition containing the microscopic three dimensional spherical structures to the skin with the applicator.

* * * * *